United States Patent [19]

Ilsink

[11] Patent Number: Plant 6,068

[45] Date of Patent: Dec. 29, 1987

[54] ROSE PLANT INTERLADA

[75] Inventor: G. Peter Ilsink, Leersum, Netherlands

[73] Assignee: Jackson & Perkins Company, Medford, Oreg.

[21] Appl. No.: 818,001

[22] Filed: Jan. 13, 1986

[51] Int. Cl.[4] ..... A01H 5/00

[52] U.S. Cl. ..... Plt./1

[58] Field of Search ..... Plt. 1

*Primary Examiner*—James R. Feyrer
*Attorney, Agent, or Firm*—Manford R. Haxton

[57] ABSTRACT

A shrub rose variety having unusually large, round flower clusters, low petal count, delicate pink color, long arching branches and good mildew resistance.

1 Drawing Figure

This present invention relates to a new and distinct variety of rose plant of the shrub class which was originated by crossing the variety Interdress, non-patented, with the variety Stad Den Helder, non-patented.

The primary objective of this breeding was to produce a new rose variety of the shrub class with profuse flowering from spring through the fall, vigorous growth and long arching canes. This objective was substantially achieved along with other desirable improvements as evidenced by the following unique combination of characteristics which are outstanding in the new variety and which distinguish it from its parents as well as from all other varieties of which I am aware:

1. Large, rounded clusters of delicately colored pink flowers;
2. A petal count of 10;
3. Long, arching branches;
4. Vigorous growth and continuous flower production; and
5. Good mildew resistance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Interdress, non-patented.

*Pollen parent.*—Stad Den Helder, non-patented.

Classification:

*Botanical.*—Rosa hybrid.

*Commercial.*—Shrub.

FLOWER

Observations made from specimens grown in a greenhouse at Irvine, Calif. in September, 1985.

Blooming habit: Recurrent.

Bud:

*Size.*—¾" when petals start to unfurl.

*Form.*—Pointed ovoid.

*Color.*—When sepals first divide, a blend of colors dominated by a pale yellow over the bottom ⅔ of the bud (Yellow Group 8C) and tipped with a rose pink color (Red Group 52C to D). The pink color extends down the petal edges; when half blown, upper side of petals is dominated by a pale pink (Red Group 39D) with an undercurrent of creamy white; lower side of petals, a pale yellow base (Yellow Group 8C) tipped or fringed with a rose pink (Red Group 52D).

*Sepals.*—Color: Green Group 138B. Three appendaged sepals lightly appendaged. Two unappendaged sepals hairy edge.

*Receptacle.*—Color: Medium green (Green Group 138B). Shape: Funnel. Size: Small. Surface: Smooth and hairy.

*Peduncle.*—Length: Short. Surface: Glandular. Color: Medium green. Strength: Stiff.

Open bloom:

*Size.*—Medium. Average open size 2½–3".

*Borne.*—In clusters.

*Stems.*—Strong.

*Form.*—When first open, flat. Permanence: Retains its form to the end.

*Petalage.*—Number of petals under normal conditions: 10.

*Color.*—Center of flower: Upper side of petals, pale pink (Red Group 39D); reverse side of petals, the pink fringe is more intense 55B to C. Base of petals, pale yellow (Yellow Group 8C). Major color: Pale pink (Red Group 39D).

*Discoloration.*—General tonality at end of first day: Some spotting or flecks due to weathering. Third day: A general fading of the pink to near white.

*Fragrance.*—Slight.

*Petals:*

*Texture.*—Thick.

*Shape.*—Round.

*Form.*—Tips slightly recurved with edges undulated.

*Arrangement.*—Imbricated. Petaloids in center, few.

*Persistance.*—Drop off cleanly.

*Lastingness.*—On the plant, fair.

Reproductive parts:

*Anthers.*—Large. Color: Yellow. Arrangement: Regular around styles.
*Filaments.*—Color: Yellow.
*Pollen.*—Gold Yellow.
*Styles.*—Color: Red.
*Stigmas.*—Color: Near white.

PLANT

Form: Arching shrub.
Growth: Very vigorous.
Foliage:
*Number of leaflets on normal mid-stem leaves.*—5–7.
*Size.*—Large.
*Quantity.*—Abundant.
*Color.*—New foliage: Reddish. Old foliage: Green (Green Group 138A).
Leaflets:
*Shape.*—Broadly oval.
*Texture.*—Smooth.
*Edge.*—Serrated.
*Serration.*—Single.

*Petiole.*—Rachis: Color: Green with reddish ridges. Underside: Rough with prickles and glands.
*Stipules.*—Medium, bearded.
*Disease resistance.*—Resistant to mildew, under normal growing conditions at Irvine, Calif.
Wood:
*New wood.*—Color: Light green. Bark: Smooth.
*Old wood.*—Color: Green. Bark: Smooth.
Prickles:
*Quantity.*—On main canes from base: Ordinary. On laterals from main canes: Ordinary.
*Form.*—Hooked downward.
*Color when young.*—Red.
Small prickles:
*Quantity.*—On main stalks, none. On laterals, none.

I claim:

1. A new and distinct variety of rose plant of the shrub class, substantially as herein shown and described, characterized particularly as to novelty by the unique combination of its unusually large, round flower clusters, low petal count, delicate pink color, long arching branches and good mildew resistance.

* * * * *

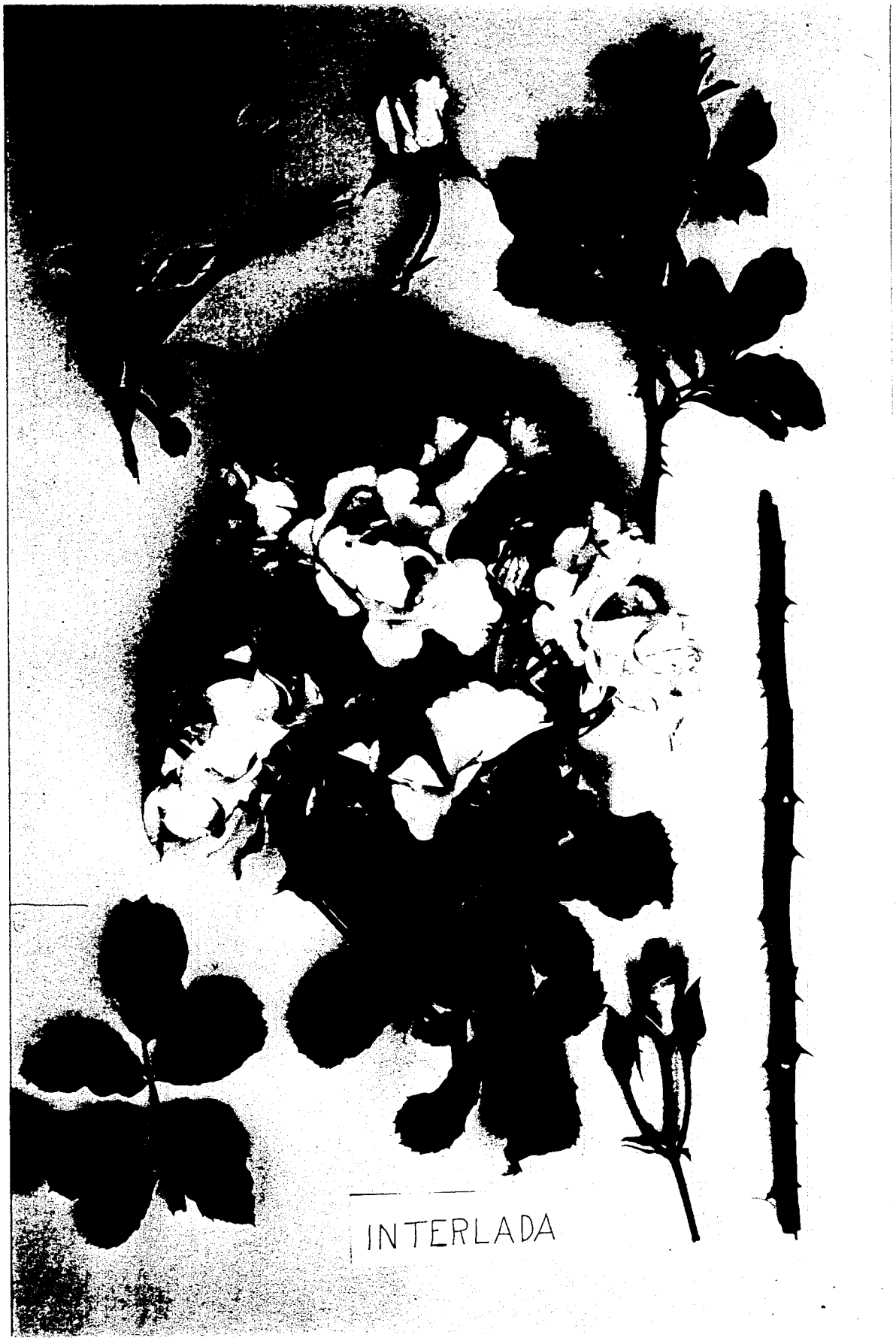
INTERLADA